United States Patent [19]

King et al.

[11] Patent Number: 5,091,534
[45] Date of Patent: Feb. 25, 1992

[54] TRIALKYLSILYL TRIFLUOROMETHANESULFONATE MEDIATED α-METHYLENIC CARBON FUNCTIONALIZATION OF 4-AZA-5α-ANDROSTAN-3-ONE STEROIDS

[75] Inventors: Anthony O. P. King, Hillsboro; Sandor Karady, Mountainside; Kevin Anderson, Plainsboro; Alan W. Douglas, Monmouth Junction; Newton L. Abramson, Edison; Richard F. Shuman, Westfield, all of N.J.

[73] Assignee: Merck & Co., Inc., Rahway, N.J.

[21] Appl. No.: 572,811

[22] Filed: Aug. 27, 1990

[51] Int. Cl.$^5$ ............................ C07J 75/00; C07J 73/00
[52] U.S. Cl. ......................................... 546/14; 546/77
[58] Field of Search ........................... 546/14, 77, 157; 552/505; 540/4

[56] References Cited

U.S. PATENT DOCUMENTS

| | | | |
|---|---|---|---|
| 4,036,831 | 10/1977 | Loken | 552/505 |
| 4,220,775 | 9/1980 | Rasmusson et al. | 548/77 |
| 4,377,584 | 5/1983 | Rasmusson et al. | 546/77 |
| 4,760,071 | 7/1988 | Rasmusson et al. | 546/77 |
| 4,859,681 | 8/1989 | Rasmusson et al. | 546/77 |

FOREIGN PATENT DOCUMENTS

| | | | |
|---|---|---|---|
| 0004949A1 | 12/1979 | European Pat. Off. | 546/77 |
| 0155096A3 | 9/1985 | European Pat. Off. | 546/77 |
| 0298652A2 | 6/1987 | European Pat. Off. | 546/77 |
| 2018257A | 10/1979 | United Kingdom | 552/505 |

OTHER PUBLICATIONS

Bhattacharya et al., Silylation-mediated oxidation . . . *J. Am. Chem. Soc.* 110, No. 10, 3318 (1988), (6).
Back, T. G. Oxidation, *J. Org. Chem.* 46, 1442 (1981).
Magnus, P. and Pappalardo, P. A. *J. Am. Chem. Soc.* 108 212 (1986).
Rasmusson et al., *J. Med. Chem.* 29, 2298 (1986), (6).
Trost and Salzmann *J. Am. Chem. Soc.* 95:20, 6840 (1973).
Emdo et al., Synthesis, 1977, pp. 867–869.
Emdo et al., Synthesis, 1977, pp. 636–637.
Schmeisser et al., Chem. Ber. 103 868–879 (1970).
Feiser and Feiser, Reggents for Organic Synthesis, vol. 8, (1980 Wiley and Sons, New York) pp. 514–515.

*Primary Examiner*—Mukund J. Shah
*Assistant Examiner*—E. C. Ward
*Attorney, Agent, or Firm*—William H. Nicholson; Robert J. North; Charles M. Caruso

[57] ABSTRACT

A novel single-pot trialkylsilyl trifluoromethanesulfonate ($R_3Si$—OTf) mediated process produces derivatives of 4-aza 3-keto steroids at the α-methylenic carbon through electrophilic substitution. These derivatives are useful in the preparation, through elimination of the substituent on the α-methylene carbon, of Δ-1 olefin 4-aza 3-keto steroids which are potent inhibitors of 5-α reductase.

8 Claims, No Drawings

TRIALKYLSILYL TRIFLUOROMETHANESULFONATE MEDIATED α-METHYLENIC CARBON FUNCTIONALIZATION OF 4-AZA-5α-ANDROSTAN-3-ONE STEROIDS

BACKGROUND OF THE INVENTION

This invention is a single-pot process for trialkylsilyl trifluoromethanesulfonate ($R_3Si$—OTf) mediated production of derivatives of 4-aza 3-keto steroids at the α-methylenic carbon through electrophilic substitution. These derivatives are useful in the preparation, through elimination of the substituent on the α-methylene carbon, of the Δ-1 olefin 4-aza 3-keto steroids, which are potent inhibitors of 5-α reductase.

The enzyme, 5-α reductase, is responsible for the local formation within a target organ of 5α-dihydrotestosterone, which is the principal mediator of androgenic activity in some organs.

Inhibitors of testosterone-5α-reductase have been shown to prevent or lessen symptoms of hyperandrogenic stimulation. Nayfe et al., [*Steroids*, 14, 269 (1969)] demonstrated in vitro that methyl 4-androsten-3-one-17β-carboxylate was a testosterone-5α-reductase inhibitor. Voigt and Hsia, [*Endocrinology*, 92, 1216 (1973), Canadian Pat. No. 970,692], demonstrated that the above ester and the parent free acid, 4-androsten-3-one-17β-carboxylic acid are both active inhibitors of testosterone-5α-reductase in vitro.

Topical application of either testosterone or 5α-dihydrotesterone caused enlargement of the female hamster flank organ, an androgen dependent sebaceous structure. However, concomitant administration of 4-androsten-3-one-17β-carboxylic acid, or its methyl ester, inhibited the response elicited by testosterone but did not inhibit the response elicited by 5α-dihydrotestosterone. These results indicated that the compounds are antiandrogenic by virtue of their ability to inhibit testosterone-5α-reductase.

A number of 4-azasteroid compounds are known. See, for example, U.S. Pat. Nos. 2,227,876; 3,239,417; 3,264,301; and 3,285,918; French Pat. No. 1,465,544; Doorenbos and Solomons, J. Pharm. Sci. 62, 4, pp. 638-640 (1973); Doorenbos and Brown, J. Pharm. Sci., 60 8, pp. 1234-1235 (1971); and Doorenbos and Kim, J. Pharm. Sci. 63, 4, pp. 620-622 (1974).

In addition, U.S. Pat. Nos. 4,377,584 and 4,220,775 of Rasmusson et al., described a group of 4-aza-17β-substituted-5α-androstan-3-ones which are said to be useful in the treatment of hyperandrogenic conditions. Furthermore, in U.S. Pat. Nos. 4,760,071, Rasmusson et al., disclosed novel 17βN-(monosubstituted) carbamoyl-4-aza-5α-androst-1-ene-3-ones, which are highly potent testosterone-5α-reductase inhibitors.

The processes known in the art for preparing the aforementioned compounds generally include a step wherein a double bond is introduced into the lactam ring of the azasteroid. Thus, selenic anhydride oxidation [Back, T. G., *J. Org. Chem.*, 46, 1442 (1981)], sulfoxide elimination [U.S. Pat. No. 4,377,584; 4,220,775], and silylation mediated DDQ (2,3-dichloro-5,6-dicyano-1,4-benzoquinone) oxidation have all been used heretofore for the introduction of the Δ-1 olefin functionality.

The instant invention discloses a method whereby a powerful silylating reagent mediates regiospecific electrophilic substitution on the lactam ring to produce a versatile array of azasteroid derivatives substituted at the α-methylenic carbon. These derivatives are useful, through elimination of the added substituents, for making the $\Delta^1$-olefin azasteroid derivative having potent 5-α reductase inhibitory activity.

SUMMARY OF THE INVENTION

The invention is a process wherein trialkylsilyl trifluoromethanesulfonate ($R_3Si$—OTf) mediates regiospecific substitution of the α-methylenic carbon of a 4-aza-5α-androstan-3-one steroid or other lactam containing compound by an electrophile, E. E is a reagent capable of appending a bromo-, iodo-, chloro-, $R^2$—S—, $R^2$—SO—, or $R^2$—NH—SO— functionality onto the α-methylenic carbon of the azasteroid. $R^2$ is a lower alkyl, perhalogenated lower alkyl, aryl, or aryl substituted lower alkyl. Aryl is phenyl, lower alkyl substituted phenyl, or halogenated phenyl, and the halogen is fluorine or chlorine. The α-methylenic substituent of an azasteroid, prepared according to the disclosed process, may be eliminated to provide the delta-1 olefinic derivative of the azasteroid which has potent 5-α reductase inhibitory activity.

OBJECTS OF THE INVENTION

Accordingly, it is an object of this invention to provide a trialkylsilyl trifluoromethanesulfonate ($R_3Si$—OTf) mediated process for electrophilic substitution of the α-methylenic carbon of 4-aza-5α-androstan-3-one steroids. Another object is to use these derivatives, produced according to the disclosed process, to prepare potent 4-aza-5α-androstan-1-ene-3-one steroid inhibitors of 5α-reductase.

DETAILED DESCRIPTION OF THE INVENTION

A novel process is disclosed wherein a lactam, and preferably a 4-aza-5α-androstan-3-one steroid, is reacted with between about a 2 to 10 fold, and preferably about a fourfold molar excess of trialkylsilyl trifluoromethanesulfonate ($R_3Si$—OTf) to generate an intermediate trialkylsilyl derivative of the azasteroid. R, the alkyl of $R_3Si$—OTf, may be comprised of from one to five carbon atoms, and in a preferred embodiment of the invention R is methyl, in which case $R_3Si$—OTf is TMSOTf (trimethylsilyl trifluoromethanesulfonate). The reaction temperature is from about $-100°$ C. to room temperature, and is preferably between about $-78°$ C. and $-20°$ C. A weak base, preferably diisopropylethylamine (DIPEA), is included in the reaction in an amount approximately equal with the amount of added $R_3Si$—OTf. The solvent is an inert, aprotic, non-polar organic, such as methylene chloride. The silylation reaction is rapid requiring about 30 minutes for completion.

Subsequent to silylation, a variety of α-methylenic derivatives of the azasteroid may be generated by electrophilic substitution with a reagent E, capable of appending a bromo-, iodo-, chloro-, $R^2$—S—, $R^2$—SO—, or $R^2$—NH—SO— functionality onto the α-methylenic carbon of the azasteroid. $R^2$ is lower alkyl, perhalogenated lower alkyl, aryl, or aryl substituted lower alkyl. Aryl is phenyl, lower alkyl substituted phenyl, or halogenated phenyl, and the halogen is fluorine or chlorine. Thus, E is a reagent selected from:

a) Ar—S—$SO_2$—Ar,
b) Ar—S—S—Ar,
c) Ar—S—Cl, d) Ar—N=S=O,
e) Ar—SO—Cl,
f) R—S—SO₂—R,
g) R—S—S—R,
h) R—S—Cl,
i) I₂,
j) Br₂, or
k) Cl₂;
wherein:
Ar is aryl and is selected from:
  a) phenyl,
  b) lower alkyl substituted phenyl, or
  c) halogenated phenyl; and
R is lower alkyl of from one to five carbons.

In a preferred embodiment of the invention, E is phenyl disulfide, trichloromethylsulfonylchloride, N-thionylaniline, bromine, or iodine.

The electrophilic reagent, E, may be added to the silylated azasteroid to generate an E' derivatized product at the α-methylenic carbon. The substitution reaction proceeds in the same pot as the silylation reaction, and isolation of the silylated intermediate is unnecessary. The solvent may be an organic solvent such as CH₂Cl₂, tolune, or tetrahydrofuran, and is preferably CH₂Cl₂, and addition of diisopropylethylamide (DIPEA) or similar base is advantageous. The reaction proceeds at temperatures between −60° C. and room temperature, and depending on the nature of the electrophile used, the process proceeds at vastly different rates. For example, halogenation and acylation with acid chlorides was very rapid while the reaction with phenyl disulfide was incomplete after 20 days.

The process may be conveniently summarized as shown in Scheme 1 below wherein a compound of formula I is converted into the trimethylsilyl intermediate II. The reaction of II with an electrophile, E, results in the formation of the compound of formula III:

SCHEME I

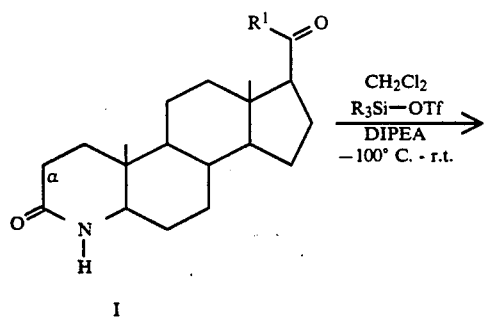

I

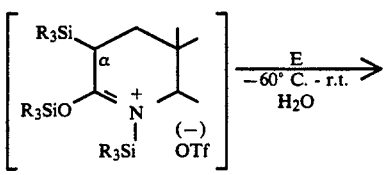

II

-continued
SCHEME I

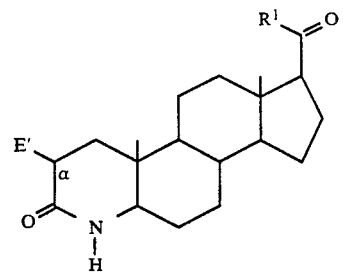

III wherein:
R is a lower alkyl of between one and five carbon atoms;
$R^1$ is:
  a) —OH,
  b) —OR, or
  c) —NHR;
E is an electrophile, as defined above, capable of appending onto the azasteroid a group, E', selected from:
  a) bromo-,
  b) iodo-,
  c) chloro-,
  d) $R^2$—S—,
  e) $R^2$—NH—S—, or
  f) $R^2$—SO—;
$R^2$ is:
  a) lower alkyl,
  b) perhalogenated lower alkyl,
  c) aryl, or
  d) aryl substituted lower alkyl;
Aryl is:
  a) phenyl,
  b) lower alkyl substituted phenyl, or
  c) halogenated phenyl; and
the halogen in a perhalogenated alkyl or halogenated phenyl is fluorine or chlorine.

When E is added as Br₂ or I₂, the Br⁺ and I⁺ ions form spontaneously and the resulting 2-iodo or 2-bromo-azasteroid may be dehydrohalogenated to generate the $\Delta^1$-olefinic azasteroid derivative. This is accomplished by using a base, for example tetrabutylammonium fluoride, 1,8-diazabicyclo[5.4.0]-7-ene (DBU), 1,5-diazabicyclo[4.3.0]none-5-ene (DBN), or 1,4-diazabicyclo[2.2.2]octane (DABCO), and preferably potassium tert-butoxide. A four to five fold excess of potassium t-butoxide in a solvent such as dimethylformamide (DMF), or dimethylsulfoxide (DMSO), generates the $\Delta^1$-azasteroid in high yield. The method should, in addition, be generally applicable in the synthesis of α-β unsaturated lactams.

In addition to dehydrohalogenation of 2-iodo- and 2-bromo- compounds, thermal elimination of C2-sulphenyl derivatives also leads to $\Delta^1$-unsaturation of the lactam. For example, "pyrolysis" of the trichloromethylsulphenyl derivative, which is achieved by boiling in acetonitrile or toluene for from 1 to 5 hours, generated the $\Delta^1$-azasteroid in 72% yield.

The following examples are provided to further illustrate the novel process herein disclosed and should not be construed as being limiting.

EXAMPLE 1

Methyl 2-phenylsulphenyl-3-oxo-4-aza-5α-androstan-17β-carboxylate

A solution of methyl-3-oxo-4-aza-5α-androstan-17β-carboxylate (1 g, 3 mmol) and DIPEA 2.1 ml, 12 mmol) in methylene chloride (20 ml) was cooled to −78° C. and trimethylsilyl trifluoromethanesulfonate (TMSOTf) (2.3 ml, 12 mmol) was added dropwise with good mixing. After this, the temperature was raised and maintained at −40° for 30 minutes. The temperature was lowered again to −78° C. Phenyl disulfide (1.3 g, 6 mmol) was added and the mixture was agitated at room temperature for 20 days. More solvent was added and the solution was extracted with HCl, saturated NaHCO$_3$ solution, and water. After drying, evaporation and flash chromatography (silica gel, CH$_2$Cl$_2$), 500 mg (38% yield) of the title compound was obtained. MP: 195°–198° C. TLC and NMR indicated that the product was a mixture of α, and β epimers.

EXAMPLE 2

Methyl 2-trichloromethylsulphenyl-3-oxo-4aza-5α-androstan-17β-carboxylate

The general procedure described in Example 1 was followed except that the reaction time was 16 hrs., and trichloromethylsulfonylchloride was added in place of phenyl disulfide. The title compound was isolated as a white powder.

$^1$H NMR (CDCl$_3$, 300 MHz): δ0.67 (s, 3H, C$_{19}$H$_3$), 0.99 (s, 3H, C$_{18}$H$_3$), 2.37 (t, 1H J=9.3H2C$_{17}$-H) 3.20 (dd, 1H, J=3.85 and 12.25 Hz, C$_6$-H), 3.68 (s, 3H, OCH$_3$), 4.13 (dd, 1H, S=9.8 and 1.09 Hz, C$_2$-H).

Anal. Calcd. C, 50.55; H, 6.06; N, 2.81; S, 6.41. Found: C, 50.50; H, 5.95; N, 2.79; S, 6.48.

EXAMPLE 3

Methyl 3-oxo-4-aza-5α-androst-1-ene-17β-carboxylate

The compound from Example 2 was converted to the Δ$^1$-azasteroid by boiling in CH$_3$CN for four hours. m.p. (decomposition): 155°–180° C.

EXAMPLE 4

Methyl-2-iodo-3-oxo-4-aza-5-α-androstane-17β-carboxylate

A solution of methyl 3-oxo 4-aza-5-α androstan-17β carboxylate (5.09 g, 0.015 mole) and DIPEA (22.0 mL, 0.23 mole) in 250 mL CH$_2$Cl$_2$ was cooled to −78° C. and TMSOTf (22.0 mL, 0.114 mole) was added dropwise and the temperature was raised to and maintained at −20° C. for 1 hr. The reaction was again cooled to −78° C., I$_2$ (18.8 g, 0.074 mole) was added and the reaction was warmed to room temperature. After 1.5 hr the reaction was extracted with 1N HCl (250 mL), 10% aqueous sodium sulfite (200 mL) and water (200 mL). The CH$_2$Cl$_2$ phase was dried over Na$_2$SO$_4$ (20 g) and the CH$_2$Cl$_2$ removed in vacuo. The solid was slurried in 60 mL CH$_3$CN, filtered and dried to give 6.06 g (88% yield) of the title compound.

$^1$H NMR (CDCl$_3$) δ6.99 (s,1H), 4.74 (dd, J=10.5, 8.0 Hz, 1H), 3.63 (s,3H), 3.14 (dd,J=12.4, 3.4 Hz, 1H), 2.56 (dd J=13.6, 8.1 Hz, 1H), 2.32 (t, J=9.1 Hz,1H), 2.2–1.9 (m,3H), 1.9–1.57 (m,4H), 1.57–0.53 (m, 9H), 0.84 (s,3H), 0.62 (s,3H).

EXAMPLE 5

N(1,1-dimethylaminoethyl)-2-bromo-3-oxo-4-aza-5α-androstane-17β-carboxamide

The same procedure was employed as given in Example 4, except bromine was used instead of iodine and the starting material was N-(1,1-dimethylaminoethyl)-3-oxo-4-aza-5α-androstane-17β-carboxamide to generate the title compound.

$^1$H NMR (CDCl$_3$): δ6.80(s,1H), 5.07(s,1H), 4.49(dd,J=10.8,7.7 Hz,1H),3.19 (dd,J=12.2,3.8 Hz,1H), 2.55. (dd,J=13.4, 7.7 Hz,1H),2.24–1.80(m,4H),1.80–1.50 (m,5H),1.50–1.12(m,5H),1.33 (s,9H), 1.12–0.78 (m, 6H), 0.88 (s,3H), 0.67 (s,3H).

$^{13}$C NMR(CDCl$_3$): δ171.55, 167.54, 60.88, 57.46, 55.46, 50.84, 46.59, 42.82, 38.32, 34.58, 29.30, 29.02, 26.89, 24.25, 23.21, 21.10, 13.19, 11.55.

Anal. Calcd.: C, 60.92; N, 6.18; H, 8.22; Br 17.62. Found: C, 61.19; N, 6.19; H, 8.11; Br, 17.70.

EXAMPLE 6

N-(1,1-dimethylethyl)-2-iodo-3-oxo-4-aza-5α-androstane-17β-carboxamide

The same procedure was used as described in Example 4, except that the starting material was as in example 5, to make the title compound which was isolated as white crystals.

$^1$H NMR (CDCl$_3$): δ7.04(s,1H), 5.09(s,1H), 4.71(dd, J=10.5, 8.1 Hz,1H), 3.11(dd, J=12.3, 3.2 Hz, 1H), 2.52 (dd, J=13.6, 8.1 Hz, 1H), 2.20–1.75 (m, 5H), 1.28 (s, 9H), 1.10–0.70 (m, 31H), 0.81 (s, 3H), 0.61 (s, 3H).

$^{13}$C NMR (CDCl$_3$): δ171.41, 168.92, 60.59, 57.18, 55.27, 50.83, 50.64, 48.73, 43.55, 39.11, 38.10, 34.51, 29.17, 28.84, 26.47, 24.09, 23.00, 20.87, 18.65, 13.01, 10.88.

Anal. Calcd.: C, 55.20; N, 5.59; H, 7.46; I, 25.36; Found: C, 55.26; N, 5.58; H, 7.54; I, 25.25.

EXAMPLE 7

N-(1,1-dimethylethyl)-3-oxo-4-aza-5-α-androst-1-ene-17-β-carboxamide

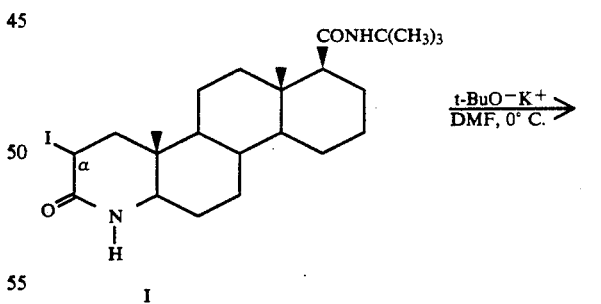

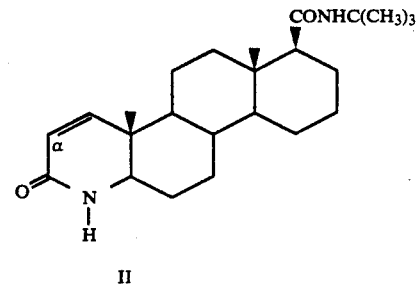

A 250-ml flask fitted with an overhead stirrer, was charged with 8.0 g ($7.1 \times 10^{-2}$ mole) of potassium t-butoxide and 20 ml of dry DMF. The t-butoxide was dissolved with stirring and the reaction cooled to $-10°$ C. A solution of 3.5 g ($7.1 \times 10^{-3}$ mole) 2-iodo-α-aza amide (I in the scheme above) in 15 ml of dry DMF was added dropwise. The mixture was stirred vigorously for 10 minutes and the reaction was quenched with the drop-wise addition of 7.2 ml ($7.1 \times 10^{-2}$ mole) of acetic acid. The reaction was stirred vigorously for 5 minutes and 200 ml of 21% sodium chloride was added slowly at 0° C. resulting in the crystallization of the Δ-1 azasteroid (II in the scheme above). The reaction was stirred overnight at 0° C. The sample was isolated by filtration and air dried under vacuum to give a free flowing solid. The sample was further dried in a vacuum oven at 60° C. to give 2.5 g of an off-white solid.

The solid was dissolved in 100 ml of isopropyl acetate and the volume was reduced to 7 ml by distillation under vacuum with heating. The sample was cooled to room temperature and 7 ml of hexanes was added slowly. The solid was stirred for 5 hours at 0° C., filtered, washed with 10 ml hexanes and dried in vacuo at 60° C. to give 2.2 g of white solid (97.2 LC wt %, 80.3% corrected yield).

The solid was dissolved in 20 ml of acetic acid and 100 ml of distilled water was added slowly. The mixture was stirred overnight at 0° C. The crystals were filtered and dried in vacuo at 60° C. to give 1.9 g of II (99+ LC wt %, 74.4% corrected yield).

$^1$H NMR (CD6$_3$) δ6.77 (d, J=10 Hz, 1H), 6.13 (bs, 4H), 5.79 (d o/d, J=10, 2. Hz, 2H), 3.35 (m, 5H), 1.34 (s, 9H), 0.96 (s, 3H), 0.69 (s, 3H).

EXAMPLE 8

Methyl-3-oxo-4-aza-5α-androst-1-ene-17-β carboxylate

The same procedure used for Example 7 was applied to methyl-2-iodo-3-oxo-4-aza-5α-androstostane 17β-carboxylate to yield the title compound.

$^1$H NMR (CDCl$_3$) δ6.8 (d, J=10 Hz), 1H), 6.1 (b.s., 1H), 5.8 (d of d, J=10 and 2 Hz, 1H), 3.65 (s, 3H), 4.35 (m, 1H), 0.95 (s, 3H), 0.65 (s, 3H).

EXAMPLE 9

2α-[phenyl(trimethylsilyl)amino]sulfinyl-3-[(trimethylsilyl)oxy]-4-aza-5-α-androstane-3-ene-17β-carboxylic acid methyl ester, and reduction to the Δ-1 azasteroid Methyl-3-Oxo-4-aza-5-α-androstane-17β-carboxylate (149.9 mg, 0.45 mmol) was dissolved in a mixture of 2.5 ml CH$_2$Cl$_2$ and 0.5 ml CD$_2$Cl$_2$. The solution was cooled in a CO$_2$-ethanol bath. TMSOTf (0.27 ml, 1.40 mmol) and DIEA (160 μl, 0.92 mmol) were added, and the solution aged overnight at $-40°$ C. $^{13}$C NMR confirmed substitution at the α-methylenic carbon with the thioaniline moiety. The solution was aged overnight at room temperature, followed by warming to 37° C. After 130 hours at 37° C., the solution was analyzed by HPLC, revealing 25% methyl 3-oxo-4-aza-5 α-androstan-1-ene-17β-carboxylate, and 35% starting lactam.

$^{13}$C-NMR (Varian Associates XL-100A operated at 25.16 MHz): δ($^{13}$C)$^{(a)}$ Cl: 31.7; C2: 60.2, 63.7; C3: 148.5, 150.0; C5: 63.2, 63.4; C6: 30.2; C7: 28.3, 28.4; C8: 34.5; C9: 51.0, —$^{(b)}$; C10: 35.7, 37.5; C11: 19.9, 20.4; C12: 37.3; C13: 43.8; C14: —$^{(b)}$; C15: 24.0; C16: 23.1; C17: —$^{(b)}$; C18: —$^{(b)}$; C19: 11.4, 11.5; C20: 174.3; C21: 51.3; 3—O—SiMe$_3$ or N—SiMe$_3$: −0.33, −0.66; Cl—: 133.6, 134.5; C2', 6', 3', 5', or 4—; 129.6, −130.5.

Notes: $^{(a)}$ Chem. shift in ppm for methylene chloride at 54.19 ppm. When diasteriomeric inequivalence was noted, two values are listed.
$^{(b)}$ Signals were obscured by solvent or other stronger peaks.

What is claimed is:

1. A process for derivatizing a lactam at the α-methylenic carbon which comprises the steps of (a) silylating the lactam with R$_3$Si—OTf, wherein R is lower alkyl, and (b) adding an electrophilic reagent, E, capable of appending a bromo-, iodo-, chloro-, R$^2$—S—, R$^2$—SO—, or R$^2$—NH—S— functionality onto the α-methylenic carbon of the lactam, wherein:
   R$^2$ is:
      a) lower alkyl,
      b) perhalogenated lower alkyl,
      c) aryl, or
      d) aryl substituted lower alkyl;
   Aryl is:
      a) phenyl,
      b) lower alkyl substituted phenyl, or
      c) halogenated phenyl; and
   the halogen in a perhalogenated alkyl or halogenated phenyl is fluorine or chlorine.

2. The process of claim 1 wherein the lactam is a 3-keto 4-azasteroid.

3. The process of claim 2 wherein E is selected from:
   a) Ar—S—SO$_2$—Ar,
   b) Ar—S—S—Ar,
   c) Ar—S—Cl,
   d) Ar—N=S=O,
   e) Ar—SO—Cl,
   f) R—S—SO$_2$—R,
   g) R—S—S—R,
   h) R—S—Cl,
   i) I$_2$,
   j) Br$_2$, or
   k) Cl$_2$;
wherein:
   Ar is aryl selected from:
      a) phenyl,
      b) lower alkyl substituted phenyl, or
      c) halogenated phenyl; and
   R is lower alkyl.

4. The process of claim 1 wherein E is:
   a) phenyl disulfide,
   b) trichloromethylsulfonylchloride,
   c) N-thionylaniline,
   d) bromine, or
   e) iodine.

5. The process of claim 3 for the preparation of Compound III:

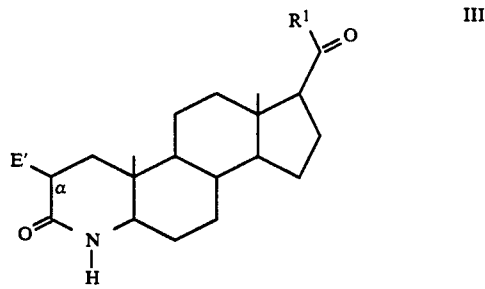

wherein:
   R$^1$ is:
      a) —OH,
      b) —OR, or
      c) —NHR;

E' is selected from:

a) bromo—, b) iodo—, c) chloro—, d) $R^2$—S—, e) $R^2$—NH—SO—, or f) $R^2$—SO—;

$R^2$ is:

a) lower alkyl, b) perhalogenated lower alkyl, c) aryl, or d) aryl substituted lower alkyl;

Aryl is:

a) phenyl, b) lower alkyl substituted phenyl, or c) halogenated phenyl; and the halogen in a perhalogenated alkyl or halogenated phenyl is fluorine or chlorine; which comprises the steps of (a) reacting a compound of formula I

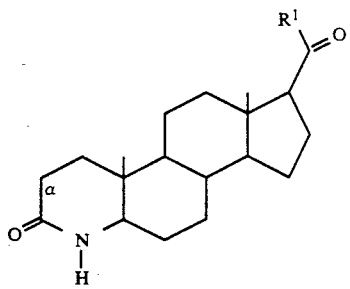

with $R_3Si$—OTf, wherein R is a lower alkyl of between one and five carbon atoms, and (b) reacting the product of step (a) with an electrophile, E.

6. The process of claim 5 wherein R is methyl.

7. The process of claim 6 which comprises the steps of (a) solubilizing the 4-aza-5α-androstan-3-one steroid in an inert, aprotic solvent, and adding between about 0.1 and 10 moles of trimethylsilyl trifluoromethanesulfonate per mole of the 4-aza-5α-androstan-3-one steroid and allowing silylation to proceed for from about five minutes to about 2 hours at a temperature of between about −100° C. and room temperature, (b) adding an electrophile, E.

8. The process of claim 7 wherein E is:
a) phenyl disulfide,
b) trichloromethylsulfonylchloride,
c) N-thionylaniline,
d) bromine, or
e) iodine.

* * * * *